United States Patent [19]
Li et al.

[11] Patent Number: 5,817,518
[45] Date of Patent: Oct. 6, 1998

[54] REAGENT AND METHOD FOR DIFFERENTIAL DETERMINATION OF LEUKOCYTES IN BLOOD

[75] Inventors: Yi Li; Carole Young; Sergio C. Veulens, all of Miami, Fla.

[73] Assignee: Coulter International Corp., Miami, Fla.

[21] Appl. No.: 573,768

[22] Filed: Dec. 18, 1995

[51] Int. Cl.$^6$ .................................................. G01N 33/48
[52] U.S. Cl. ................................. 436/63; 436/8; 436/10; 436/17; 436/164; 436/166; 436/171; 436/175; 252/408.1; 435/2
[58] Field of Search ................................... 436/8, 10, 17, 436/18, 63, 164, 166, 171, 172, 175, 176; 435/2; 252/408.1

[56] References Cited

U.S. PATENT DOCUMENTS

| | | | |
|---|---|---|---|
| 2,656,508 | 10/1953 | Coulter | 324/71.1 |
| 4,298,836 | 11/1981 | Groves et al. | 324/71.1 |
| 4,330,341 | 5/1982 | May et al. | 106/308 N |
| 4,485,175 | 11/1984 | Ledis et al. | 436/17 |
| 4,751,179 | 6/1988 | Ledis et al. | 435/34 |
| 5,116,539 | 5/1992 | Hamaguchi et al. | 252/408.1 |
| 5,125,737 | 6/1992 | Rodriguez et al. | 356/39 |
| 5,155,044 | 10/1992 | Ledis et al. | 436/63 |
| 5,196,346 | 3/1993 | Lefevre et al. | 436/63 |
| 5,232,857 | 8/1993 | Lefevre et al. | 436/10 |
| 5,389,549 | 2/1995 | Hamaguchi et al. | 436/10 |
| 5,496,734 | 3/1996 | Sakata | 436/63 |
| 5,510,267 | 4/1996 | Marshall | 436/63 |
| 5,538,893 | 7/1996 | Sakata et al. | 436/10 |

*Primary Examiner*—Maureen M. Wallenhorst
*Attorney, Agent, or Firm*—Mitchell E. Alter

[57] ABSTRACT

This invention relates to a lytic reagent and a method of using the lytic reagent for automatically determining leukocyte subpopulations in blood. More specifically, the new lytic reagent lyses red blood cells and affects the eosinophils which enables the differentiation of at least one subpopulation of leukocytes. The lytic reagent is an acidic, hypertonic aqueous solution containing alkali metal salt of alkyl sulfite, an eosinolytic agent, a nonionic surfactant and a physiological salt. When used in combination with a second lytic reagent system, one is able to obtain at least a five part differential of leukocytes using DC and RF measurements.

31 Claims, 4 Drawing Sheets

REAGENT AND METHOD FOR DIFFERENTIAL DETERMINATION OF LEUKOCYTES IN BLOOD

FIELD OF THE INVENTION

The present invention relates to a lytic reagent and a method for differentiation of leukocyte subpopulations of blood samples by means of suitable electronic instruments.

BACKGROUND OF THE INVENTION

Analysis of leukocyte populations from blood samples is an integral and essential part of diagnostic procedures regarding a multiplicity of pathologies. Measurements of eosinophils which are a subpopulation of leukocytes are important to the diagnosis of several diseases. For instance, an increase in the number of eosinophils is found in Hodgkin's disease, parasitic and allergic diseases.

Traditional analysis of blood samples involves the smearing of a blood sample on a microscope slide, followed by an visual analysis of the slide. This approach is extremely time consuming as well as being subject to the interpretation of the individual analyzing the slide. These factors have led to the development of automated leukocyte analysis utilizing flow cytometry. An essential step in leukocyte analysis using automated hematology instruments is the lysis of the red blood cells. Thus far, several lytic reagents have been developed for use with whole blood samples.

U.S. Pat. No. 4,485,175 (to Ledis et al.) describes a reagent system and method for performing differential leukocyte determinations into three subpopulations utilizing automated cell counting equipment. This reagent system contains a blood diluent and a lytic reagent. The lytic reagent comprises a mixture of quaternary ammonium surfactants. However, this reagent system, has its application to effect differentiation of the leukocytes into only three subpopulations: lymphocytes, monocytes and granulocytes. The reagent system was not able to further differentiate granulocytes into more than three subpopulations.

U.S. Pat. No. 4,751,179 (to Ledis et al.) discloses a reagent system and method for performing differential determinations of leukocytes utilizing automated cell counting equipment. This reagent system comprises: 1) a lysing reagent comprising either a single lytic diluent containing saponin or two solutions to be added sequentially consisting of a prediluent and a lytic reagent containing saponin; and 2) an active cross linking agent such as glutaraldehyde as a fixing reagent. After heating the blood sample lytic reagent system mixture and analyzing it by DC and Opacity, four subpopulations of leukocytes can be determined. These four subpopulations are lymphocytes, monocytes, neutrophils and eosinophils. This method requires heating of the sample mixture at 60° C. to 75° C. prior to measurement by an instrument.

U.S. Pat. No. 5,155,044 (to Ledis et al.) discloses a reagent system and method for the rapid isolation and analysis of leukocytes from a whole blood sample and enables automated differentiation into five subpopulations using an automated hematology analyzer capable of Conductivity (DC), Radio Frequency (RF) and Light Scatter (LS) measurements. The reagent system is composed of an aqueous lytic reagent which comprises an acid, or a mixture of acid and saponin, and an aqueous salt quench solution. This method is rapid and provides a five part leukocyte differential of a whole blood sample in a single step measurement. The single step measurement is performed with a single aliquot of a blood sample with the same lytic reagent system obtain a differentiation of the leukocytes. However, using this reagent and method to achieve differentiation of leukocytes into five subpopulations requires sophisticated and expensive laser devices. If only DC and RF detections are utilized with this reagent system, the granulocyte subpopulations will not be adequately differentiated into basophil, eosinophil and neutrophil subpopulations. The granulocytes are not differentiated because the DC and RF signals of the subpopulations overlap among each other under the conditions revealed by this patent.

Another approach for differentiation of leukocytes into four or five subpopulations utilizing RF and DC measurements is to use multiple reagents and multiple measurements. Separate reagents are used for differentiating the specific subpopulations. Typically, a first lytic reagent, like the ones revealed in U.S. Pat. No. 5,116,539 (to Hamaguchi et al.) and U.S. Pat. No. 5,389,549 (to Hamaguchi et al.) are used to differentiate the leukocytes into three subpopulations (i.e., monocytes, lymphocytes and granulocytes) using DC and RF measurements.

In U.S. Pat. No. 5,116,539, an additional lytic reagent is used with an additional measurement to obtain the eosinophil subpopulation. This enables a four part differentiation of lymphocytes, monocytes, eosinophils and the remaining granulocytes. The lytic reagent is a hypotonic aqueous solution composed of a polyoxyethylene-based nonionic surfactant and a buffer to adjust the pH of the solution within the range of 3–11. The lytic reagent lyses not only red blood cells but also the leukocytes except eosinophils so that the eosinophils can be counted based on their remaining cellular volume. However, to achieve eosinophil separations the method of using the lytic reagent requires incubation of the sample mixture at 40° C. for a period of 50 seconds. This elevated temperature requirement necessitated instrumentation which is significantly more complex because the reactions must be thermostatically controlled. In addition, the extended reaction time directly decreases the throughput of the automated analyzer.

In U.S. Pat. No. 5,389,549, two additional lytic reagents are needed and two additional measurements are required to obtain the eosinophil and basophil subpopulations so as to provide a five part differential. In this disclosure, the total eosinophil and basophil subpopulations obtained from separate measurements are subtracted from the total granulocyte population to obtain the neutrophil subpopulation.

U.S. Pat. No. 5,196,346 (to Lefevre et al.) discloses a lytic reagent and method of using the same for automated determination of basophils in whole blood samples by lysing all blood cells, including both erythrocytes and leukocytes, with the exception of the basophils. The lytic reagent was composed of a polyoxyethylene ether-type surfactant, a phthalic acid/HCl mixture, sodium dodecyl sulfate (SDS) and a butylated hydroxytoluene-type antioxidizing agent. SDS was used as a protein denaturing agent to reduce the formation of deposits in the measuring instrument and was also found to accelerate the lysis of the cells. The disclosed method requires a thermostatically controlled reaction temperature between 30° to 40° C. and is limited to the counting of only basophils.

Pending U.S. patent application Ser. No. 08/488,630 filed Jun. 8, 1995 discloses a lytic reagent system and a method for automated differentiation of leukocytes into five subpopulations using DC, RF and light scatter measurement devices. The lytic reagent system is composed of an aqueous lytic reagent which comprises an ethoxylated long chain amine compound and an acid, and a stabilizing reagent which comprises a hypertonic, alkaline reagent composition. The disclosed lytic reagent system provides a five part leukocyte differential using a single measurement when DC, RF and light scatter measurements are used. However, if the lytic reagent system is used on a hematology analyzer equipped with only DC and RF measurement devices, only four subpopulations can be obtained, i.e., monocytes, lymphocytes, basophils, and the sum of neutrophils and eosinophils.

In addition, pending U.S. patent application Ser. No. 08/496,469 filed Jun. 29, 1995 discloses a lytic reagent system and a method for automated differentiation of leukocytes into five subpopulations using DC, RF and light scatter measurement devices. The lytic reagent system is composed of an aqueous lytic reagent which comprises a polyoxyethylene based surfactant and an acid, and a hypertonic, alkaline stabilizing reagent composition. The disclosed lytic reagent system also provides a five part leukocyte differential using a single measurement when DC, RF and light scatter measurements are used. However, if the lytic reagent system is used on a hematology analyzer equipped with only DC and RF measurement devices, only four subpopulations can be obtained, i.e., monocytes, lymphocytes, basophils, and the sum of neutrophils and eosinophils.

SUMMARY OF THE INVENTION

This invention relates to a new lytic reagent composition. The lytic reagent composition is an acidic, hypertonic aqueous solution comprising an alkali metal salt of alkyl sulfate, an eosinolytic agent, a nonionic surfactant and a physiological salt. The new lytic reagent composition can lyse red blood cells and selectively affect and separate the eosinophil subpopulation from the other granulocyte subpopulations by selectively shrinking the eosinophils. This enables the differentiation of at least one of the subpopulations of leukocytes.

The lytic reagent composition provides an advantage of operating entirely at room temperature. For adequate separation of the eosinophil subpopulation, prior art lysis operated at elevated temperatures, 30° C. or higher. This elevated temperature requirement necessitated analysis instrumentation which was significantly more complex because the reactions had to be thermostatically controlled. The present invention overcomes the need for thermostatic control by operating optimally at room temperature.

In addition, the invention relates to a method of using the lytic reagent composition for automatically determining leukocyte subpopulations in blood. The method of the present invention comprises exposing a blood sample to a lytic reagent composition, incubating the sample mixture at room temperature for less than 25 seconds and analyzing the sample mixture with an automated hematology instrument. The synergetic effect of the surface active agents provides a rapid and selective action against the eosinophil subpopulation, which allows a rapid separation of the eosinophil subpopulation from other leukocyte subpopulations by means of simple DC and RF measurements. Moreover, the method provides the advantage of eliminating the need of an expensive laser device to determine the eosinophil subpopulation.

Still further, the present invention relates to a method of using the new lytic reagent composition in combination with a second lytic reagent system to obtain at least a five part differential of leukocytes using only DC and RF measurements.

BRIEF DESCRIPTION OF THE DRAWINGS

FIGS. 1a and 1b display the eosinophil differentiation of a normal whole blood sample processed as described in Example I.

DETAILED DESCRIPTION OF THE INVENTION

The present invention relates to an aqueous lytic reagent composition and a method for the rapid differentiation of at least one leukocyte subpopulations by DC and RF measurements. The lytic reagent composition lyses red blood cells and selectively shrinks the eosinophil subpopulation from the other granulocyte subpopulation. Moreover, the lytic reagent and the method of using the lytic reagent enables the differentiation and enumeration of the eosinophils without using laser measurements based on the differences in volume after exposure of the blood sample to the lytic reagent composition. In addition, a method is provided for the differentiation of at least five leukocyte subpopulations using only DC and RF measurements.

In the first embodiment of the present invention, the aqueous lytic reagent composition comprises an alkali metal salt of alkyl sulfates, an acid, an eosinolytic agent that facilitates the selective shrinkage of the eosinophil subpopulation selected from the group consisting of organic phosphate esters, alkali metal salts of the organic phosphate esters, ethoxylated phosphate esters, ethoxylated mercaptans, ethoxylated lanolin alcohols, ethoxylated alkyl phenols, ethoxylated alkyl alcohols, ethoxylated alkenyl alcohols and mixtures thereof, a nonionic surfactant that protects the neutrophil subpopulation from lysis, and a physiological salt sufficient to adjust the osmolality of said lytic reagent composition between 370 to 720 mOsm. The synergetic effect of these membrane active chemicals enables the lytic reagent to rapidly lyse red blood cells and to concurrently selectively shrink and differentiate the eosinophils from other subpopulations of the leukocytes.

The function of the alkali metal salt of alkyl sulfates in the lytic reagent of the present invention is crucial. It lyses the red blood cells providing the opportunity for leukocyte differential analysis. In addition, it also selectively affects the eosinophil subpopulation cell membrane and shrinks the cell volume down rapidly. The alkyl chain length of the alkali salt of alkyl sulfates is from 10 to 18 carbon atoms, preferably 12 to 14 carbon atoms. Preferred examples of the alkali salt of alkyl sulfates include sodium dodecyl sulfate and sodium tetradecyl sulfate. Most preferably sodium dodecyl sulfate is employed. The concentration of the alkali salts of alkyl sulfate is from about 0.02% to about 0.16%, preferably from about 0.04% to 0.12% (w/v).

The function of the acid is to assist the selective lysing of the red blood cells and provide an acidic environment for selective shrinkage of the eosinophil subpopulation. It has been found that the selective shrinkage of the eosinophil subpopulation occurs only in an acidic medium.

A broad range of acids can be utilized in the present invention. However, those having pK below 3 are preferably used. The acids can be an organic acid, an inorganic acid, or a mixture thereof. The examples of suitable acids in the lytic reagent of the present invention are acetic acid, citric acid, formic acid, propionic, hydrochloric, phosphoric acid, sulfuric acid and mixtures thereof.

The amount of the acid needs to be sufficient for rapid lysing of red blood cells, while not causing damage of the other granulocyte subpopulations. The pH of the lytic reagent should remain within a range from about 1.4 to about 3.4, preferably about 1.8 to about 2.6.

A group of surfactants function as eosinolytic agents. Their presence in the lytic reagent composition assists in the shrinkage of the eosinophils and also helps the shrunken eosinophils to form a distinct cluster for differential analysis. These eosinolytic agents comprise organic phosphate esters, alkali metal salts of the organic phosphate esters, ethoxylated phosphate esters, ethoxylated mercaptans, ethoxylated lanolin alcohols, ethoxylated alkyl phenols, ethoxylated alkyl alcohols, ethoxylated alkenyl alcohols and mixture thereof.

Because of significantly different chemical natures of these surfactants, the mode of their action under the conditions of this invention is presently unknown. In general, the nonionic eosinolytic agents have a hydrophile lipophile balance (HLB) which is less than about 15. The nonionic eosinolytic agents are known to be strong to moderate erythrolytic agents in a broad pH range. However, this does not explain their selective effects on the eosinophil cytoplasm membranes and their ability to differentiate the eosinophil subpopulation from other granulocyte subpopulations. The concentration of the eosinolytic agents ranges from 0.05% to 0.8% (w/v) depending on the potency of the specific chemical used, which can be determined empirically.

Another group of nonionic surfactants function as leukoprotective agents. The leukoprotective agent has two functions. One function is to assist the selective red blood cell lysing. The second function is to protect the leukocytes, especially the neutrophil subpopulation, from damage during the lytic reaction. Suitable examples comprise ethoxylated alkyl alcohol or ethoxylated alkenyl alcohol and mixture thereof having a HLB of 16 or greater.

If the neutrophil subpopulation is affected by the lytic reagent during the analysis, they will also shrink in size and interfere with the eosinophil classification. However, if an excess amount of the leukoprotective agent is used, the eosinophil subpopulation separation would take place only with an extended reaction time of typically greater than approximately 45 seconds, or become practically unachievable. Therefore, an appropriate concentration of the leukoprotective agent, which can be determined experimentally, is desired. The concentration of the ethoxylated alkyl alcohol or ethoxylated alkenyl alcohol is from about 0.5 to about 3%, preferably from about 0.8% to about 2% (w/v).

A physiological salt is used to adjust the osmolality of the lytic reagent composition. It has been found by the inventors that eosinophil shrinkage only occurs in a hypertonic environment in the range from about 370 to 720 mOsm, and preferably from about 400 to 570 mOsm. In a preferred embodiment, alkali metal salts of chloride and sulfate are used for this purpose. With an appropriate combination of the alkali metal salts of chloride and sulfate, the shrinkage of the eosinophils takes place rapidly and the shrunken eosinophils form a distinct population.

Suitable examples of the physiological salts include sodium or potassium chloride and sodium or potassium sulfate. The concentration of the alkali metal salts of chloride ranges from about 0.1% to about 1.2%, preferably from about 0.3% to about 1.0% (w/v). The concentration of the alkali metal salts of sulfate ranges from about 0.4% to about 2%, preferably from about 0.6% to about 1.5% (w/v).

Optionally, polyoxyethylene and polyoxypropylene copolymers can be used to assist dissolving the red blood cell debris and to reduce the noise generated from the debris. In addition, it has been found that the copolymers can assist the eosinophil subpopulation to form a distinct cluster. A preferred embodiment of the present invention utilizes Pluronic copolymers (manufactured by BASF Corporation, Parsippany, N.J.), such as Pluronic 10R5 and Pluronic L35.

Additional optional additives can also be included in the lytic reagent composition in concentrations that their presence is compatible with the primary functional components of the lytic reagent composition. Among these additives are preservatives which have anti-oxidant properties, to increase the shelf-life of the composition, and which have antimicrobial properties. Preservatives which have anti-oxidant properties include but are not limited to EDTA and butylmethylphenol. Preservatives which have anti-microbial activity include but are not limited to dimethyloldimethyl hydantoin and isothiozolone derivatives.

In a second embodiment of the present invention, a method for lysis of red blood cells in a blood sample and analysis of the remaining leukocyte subpopulations is provided. The method comprises the steps of: step 1) exposing a blood sample to a lytic reagent composition for a time sufficient to lyse red blood cells and separate at least one leukocyte subpopulations in said blood sample, said lytic reagent comprising an alkali metal salt of alkyl sulfates, an acid, an eosinolytic agent that facilitates the selective shrinkage of the eosinophil subpopulation selected from the group consisting of organic phosphate esters, alkali metal salts of the organic phosphate esters, ethoxylated phosphate esters, ethoxylated mercaptans, ethoxylated lanolin alcohols, ethoxylated alkyl phenols, ethoxylated alkyl alcohols, ethoxylated alkenyl alcohols and mixtures thereof, a nonionic surfactant that protects the neutrophil subpopulation from lysis, and a physiological salt sufficient to adjust the osmolality of said lytic reagent composition between 370 to 720 mOsm, step 2) differentiating at least one leukocyte subpopulation selected from the group consisting of eosinophils, lymphocytes, monocytes, and neutrophils, and step 3) reporting results of said differentiation.

The blood sample is exposed to a lytic reagent composition for a time sufficient to lyse red blood cells and separate at least one leukocyte subpopulation in said blood sample. The blood sample is exposed to the lytic reagent by mixing the lytic reagent with a blood sample so that the blood sample is diluted approximately 45 to 70 fold. The diluted sample mixture is incubated at room temperature. Preferably the temperature will be between approximately 15° to 30° C. The incubation time is approximately 10 to 25 seconds, preferably less than 18 seconds. The sample mixture is analyzed with an automated hematology instrument. The instrument measures and differentiates at least one leukocyte subpopulation, preferably the eosinophil or neutrophil subpopulations, and most preferably the eosinophil subpopulation.

The differential is performed using at least two types of measurements selected from the group consisting of DC, RF and light scatter measurements. Preferably the differentiating is performed using only DC and RF measurements. The DC method detects any change that occurs in electric current on account of the difference in conductivity between particles and the fluid medium when a sample mixture is allowed to pass through a narrow fluid channel. In the DC method, the intensity of a signal detected is essentially proportional to the volume of particles. In the RF method, a sample mixture is allowed to pass through a fluid channel between closely adjacent electrodes and the change that occurs in the electric impedance between the electrodes on account of the difference in dielectric constant between the particles and the fluid medium is detected. In the RF method, the intensity of a signal detected reflects information related to the structure of the particles and the nature of the material of which they are made. Details of the DC and RF detection principles and techniques are taught in U.S. Pat. No. 2,656,508 assigned to Coulter Electronics, Inc. and U.S. Pat. No. 4,298,836 assigned to Coulter Electronics, Inc.

The method using the lytic reagent composition of the present invention for leukocyte differential analysis of a blood sample provides a rapid method using one lytic reagent. The lytic reagent composition lyses the red blood cells and selectively affects the cytoplasm membrane of the eosinophil subpopulation and shrinks the eosinophil subpopulation cell volumes. The granulocytes other than the eosinophils remain essentially intact during the lytic reaction.

Figure 1A:
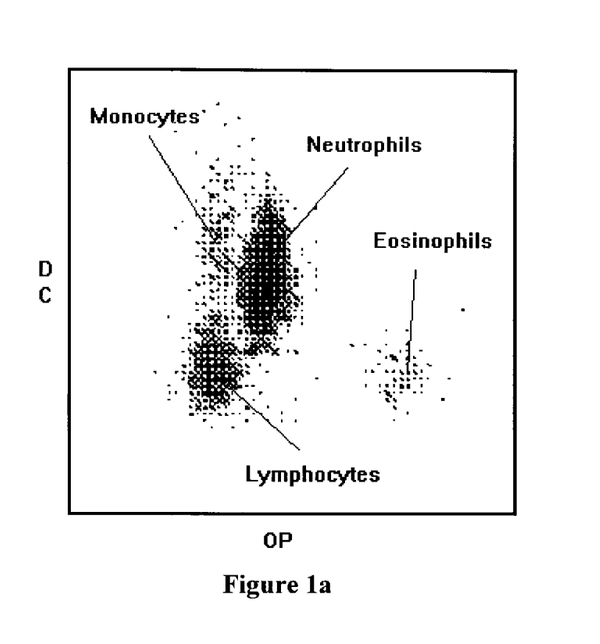
FIG. 1a shows a two dimensional diagram of DC vs. OP (Opacity, a function of RF and DC)
Figure 1B:
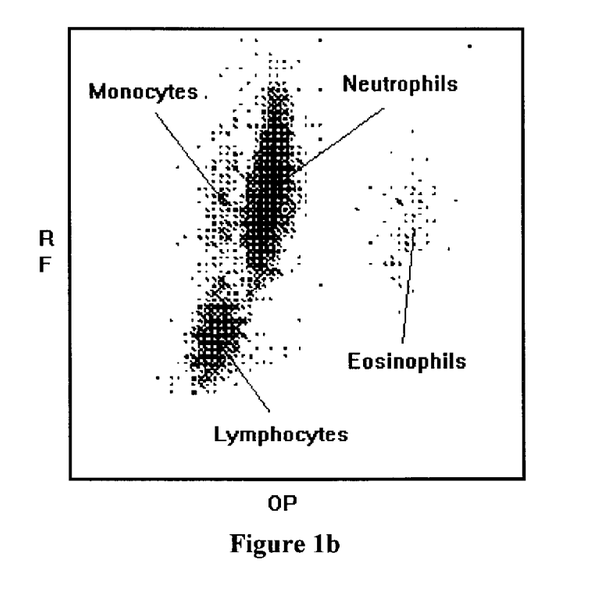
FIG. 1b shows the diagram of RF vs. OP, respectively. Leukocyte subpopulations are shown as labeled.

Example I illustrates the application of a preferred embodiment of the disclosed lytic reagent composition for leukocyte differentiation and enumeration of a whole blood sample. FIGS. 1a and 1b show the differential analysis of a whole blood sample processed as described in Example I using DC and RF measurements. The cells flow through an aperture where an impedance measuring device records the responses of the cells to radio frequency and direct current. The electrical signals are processed and plotted as two dimensional diagrams, DC vs. Opacity or RF vs. Opacity as illustrated in FIG. 1a and 1b, respectively. As shown, after exposure of a blood sample to the lytic reagent composition of the present invention, the eosinophil subpopulation is completely separated from other leukocyte populations. Although this example is conducted with a non-focused flow instrument, the same results would be obtained using a focused flow system as shown in FIG. 2.

It is noted that although the size of eosinophils were reduced dramatically after their exposure to the lytic reagent, their RF signals were not perceptibly affected. The differentiation between the neutrophils and the eosinophils using the DC and RF detection technique is mainly achieved through their significant difference in size and through Opacity. As illustrated in both FIGS. 1a and 1b, the eosinophil subpopulation had a right shift in opacity and moved away completely from the neutrophils and other leukocyte subpopulations.

Figure 2:
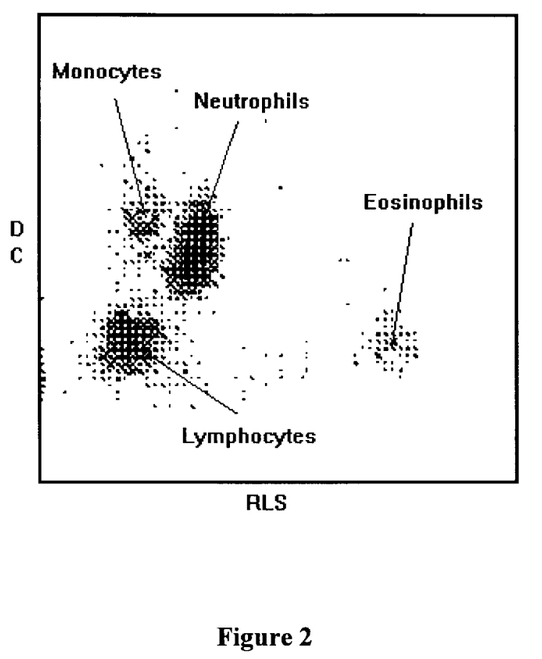
FIG. 2 displays a DC vs. Rotated light scatter (RLS) diagram of a whole blood sample processed as described in Example I, except analyzed on an experimental hematology analyzer equipped with DC, RF and light scatter devices utilizing a focused flow method.

FIG. 2 shows the confirmation of the eosinophil classification of the present invention by a DC vs. rotated light scatter diagram using the same blood sample processed as described in Example I on an experimental hematology analyzer equipped with DC, RF and light scatter devices utilizing a focused flow method. In DC vs. light scatter dimension the eosinophils are separated from neutrophils by both their size and light scatter differences. The number of cells classified as eosinophils by the method of the present invention was consistent with the number of eosinophils counted by the conventional manual method.

In a third embodiment of the present invention, a method is provided for lysis of red blood cells in a blood sample and analysis of the remaining leukocyte subpopulations into at least five subpopulations of leukocytes. The method comprises the steps of: step 1) treating a first aliquot of a blood sample with a first lytic reagent composition for a time sufficient to lyse red blood cells and separate at least one leukocyte subpopulation in said blood sample, step 2) treating a second aliquot of said blood sample with a second lytic reagent system sufficient to lyse red blood cells and separate four leukocyte subpopulations in said blood sample, step 3) analyzing the first aliquot of said treated blood using DC and RF measurements, step 4) analyzing the second aliquot of said treated blood using DC and RF measurements, and step 5) reporting at least five subpopulations of leukocytes.

Step 1 which treats a first aliquot of blood is accomplished using the lytic reagent composition described in the first embodiment of this invention. Step 3 which is directed to analyzing the first aliquot of blood is accomplished by the method described in the second embodiment of this invention.

Step 2 is accomplished by treating a second aliquot of the blood sample with a second lytic reagent system sufficient to lyse red blood cells and separate four leukocyte subpopulations in the blood sample. The second lytic reagent system separates the leukocytes into the lymphocyte, monocyte, basophil and granulocytes other than basophil subpopulation. The blood sample is exposed to the second lytic reagent for less than 10 seconds.

The second lytic reagent system typically will include a lytic reagent and a stabilizing reagent composition. An example of a second lytic reagent system comprises a lytic reagent comprising an ethoxylated long chain amine compound represented by the general formula:

wherein R is an alkyl alkenyl or alkynyl group having 12 to 22 carbon atoms, m and n are each 1 or more and m+n is between 20 and 40; and an acid to adjust the pH of the lytic reagent to be within the range of 2.0 to 3.6; and a hypertonic, alkaline stabilizing reagent composition. Preferably, R is an alkyl group having 14 to 20 carbon atoms. In addition, it is preferred that the acid used to adjust the pH comprises an organic acid. Most preferably the acid used to adjust the pH comprises an effective mixture of formic acid and an acid selected from the group consisting of acetic, citric, oxalic, glycolic, propionic, hydrochloric, sulfuric and phosphoric acid and mixtures thereof.

Another example of a second lytic reagent system comprises a lytic reagent comprising a polyoxyethylene based surfactant represented by the general formula:

wherein $R_1$ is an alkyl, alkenyl or alkynyl group having 10 to 22 carbon atoms, $R_2$ is —O— or —COO—, and n is between 20 and 35; and an acid to adjust the pH of the lytic reagent composition to be within the range of 2.0 to 4.0, and a hypertonic, alkaline stabilizing reagent composition. Preferably R is an alkyl group having 12 to 20 carbon atoms. In addition, it is preferred that the acid used to adjust the pH comprises an organic acid. Most preferably the acid used to adjust the pH comprises an effective mixture of formic acid and an acid selected from the group consisting of acetic, citric, oxalic, glycolic, propionic, hydrochloric, sulfuric and phosphoric acid and mixtures thereof.

Two examples of the second lytic reagent are provided in Examples IV and V. An example of a stabilizing reagent that is used with the second lytic reagents of Example IV and V is provided in Example VI.

Figure 4:
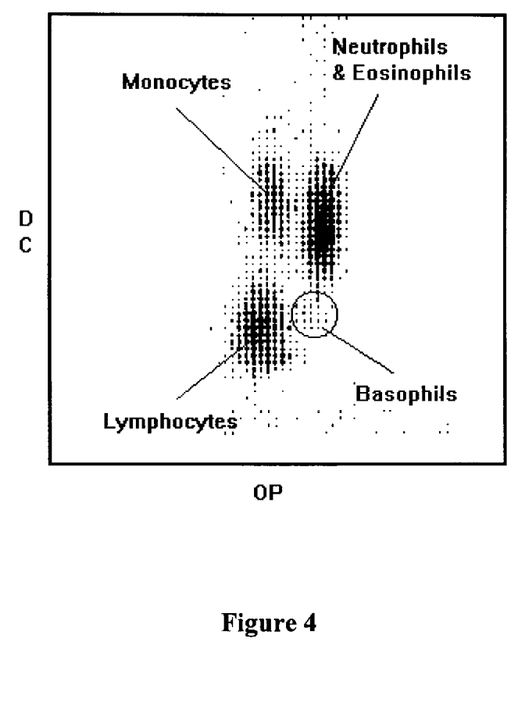
FIG. 4 displays the two dimensional diagrams of whole blood samples using an example of the second lytic reagent described in Example IV and the stabilizing reagent described in Example VI and processed in accordance with Example VII. Each cluster represents one or more leukocyte subpopulations as labeled.

Step 4 is accomplished by analyzing the second aliquot of the lysed blood using DC and RF. FIG. 4 depicts the four leukocyte subpopulations that were obtained using the second lytic reagent described in Example IV and the stabilizing reagent composition described in Example VI from a blood sample analyzed as described in the method of Example VII. As shown in FIG. 4, the four leukocyte subpopulations of lymphocytes, monocytes, basophils and granulocytes other than basophils are clearly separated using DC and RF measurements.

Step 5 reports at least five subpopulations of leukocytes. As noted above, the lymphocytes, monocytes, basophils are directly obtained in step 4. The neutrophil subpopulation is obtained by subtracting the eosinophil subpopulation obtained in step 3 from the granulocytes obtained in step 4.

The lytic reagent composition, second lytic reagent system, or a combination thereof can each be sold as a kit wherein the lytic reagent is packed in a container, such as a plastic container. Instructions on how to use these components in accordance with the present invention are preferably included inside or on the container.

The invention is further described by reference to the following examples, which are intended to be illustrative and not limiting.

EXAMPLE I

| | |
|---|---|
| 1. T-mulz 66H (Harcros Chemicals, Inc., 50% potassium salt of organic phosphate esters) | 5.0 g |
| 2. Sodium dodecylsulfate | 1.0 g |
| 3. Hetoxol STA30 (Heterene, ethoxylated stearyl alcohol) | 10.0 g |
| 4. Pluronic 10R5 (BASF) | 15.0 g |
| 5. Formic acid | 0.2 ml |
| 6. Sodium sulfate | 9.0 g |
| 7. Potassium chloride | 6.0 g |
| 8. BHT predissolved in ethanol | 0.05 g |
| 9. Proclin 300 (Rohm & Haas Co.) | 0.5 ml |
| 10. pH (adjusted by 4M HCl) | 2.2 |
| 11. Deionized water | adjusted to 1L |

To 28 ml of an EDTA-anti-coagulated normal whole blood sample, 1800 ml of the lytic reagent composition was added and the mixture was gently mixed by swirling for 9 seconds at room temperature (approximately 21° C.), and was ready for differential analysis about 13 seconds after the addition of the lytic reagent composition. The blood mixture was kept at acidic (pH about 2.2) and hypertonic conditions with an osmolality of 484 mOsm. A differential analysis was performed on an experimental hematology analyzer equipped with DC and RF devices utilizing a non-focused flow technique. The resulting two-dimensional diagrams are illustrated in FIGS. 1a and 1b. The vertical and horizontal axes of FIG. 1a are DC and Opacity, respectively, and the vertical and horizontal axes of FIG. 1b are RF and Opacity, respectively. The eosinophil populations are differentiated and enumerated, and reported as either absolute count or as percentage when calculated versus the total leukocyte counts.

EXAMPLE II

Figure 3A:
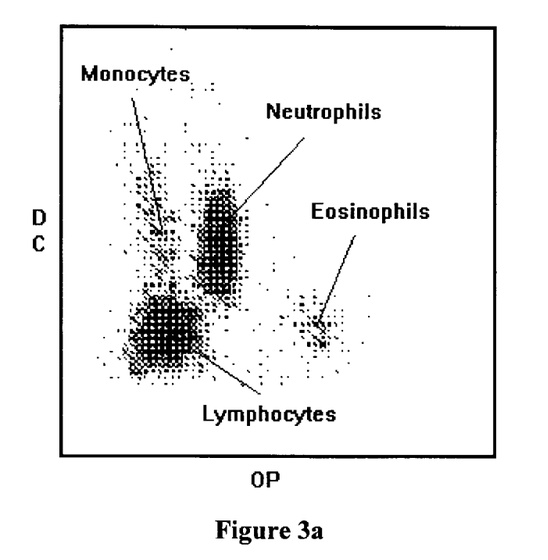
FIGS. 3a and 3b display the two dimensional diagrams of whole blood samples processed as described in Example II using an example of the lytic reagent composition of the present invention.
Figure 3B:
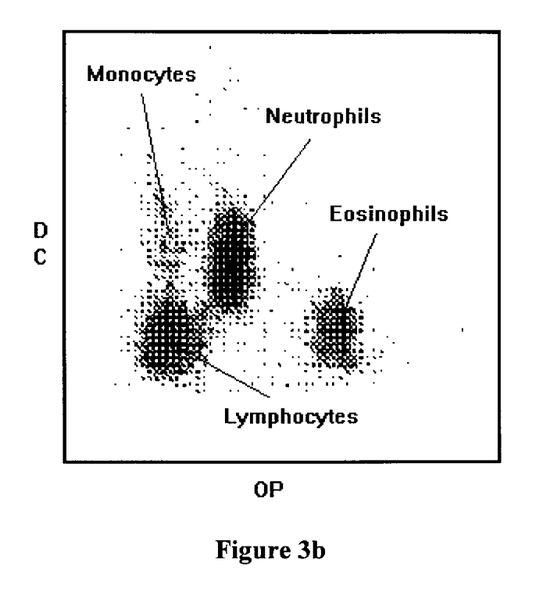

A lytic reagent composition formulated with the following composition was used for the differential analysis of the subpopulations of leukocytes. To 28 ml of an EDTA-anti-coagulated whole blood sample, 1600 ml of the lytic reagent composition was added and the mixture was gently mixed by swirling for about 8 seconds at room temperature (approximately 21° C.), and was ready for differential analysis about 12 seconds after the addition of the lytic reagent composition. FIGS. 3a and 3b show two DC vs. Opacity diagrams. FIG. 3a corresponds to a normal blood sample and FIG. 3b corresponds to a blood sample with elevated eosinophils (12% from manual differential count).

| | |
|---|---|
| 1. Burco TME (Burlington Chemical Co. Inc., ethoxylated dodecylmercaptan, HLB = 13.0) | 1.5 g |
| 2. Sodium dodecylsulfate | 1.0 g |
| 3. Hetoxol STA30 (Heterene, ethoxylated stearyl alcohol) | 8.0 g |
| 4. Pluronic L35 (BASF) | 10.0 g |
| 5. Citric acid | 17.0ml |
| 6. Sodium sulfate | 9.0 g |
| 7. Potassium chloride | 6.0 g |
| 8. Deionized water | adjusted to 1 L |
| 9. pH | 2.2 |

EXAMPLE III

A lytic reagent was formulated using the following composition. The reagent was used for the differential analysis of the subpopulations of leukocytes. To 28 ml of an EDTA-anti-coagulated normal whole blood sample, approximately 1880 ml of the lytic reagent composition was added and the mixture was gently mixed by swirling for 11 seconds at room temperature (approximately 21° C.), and was ready for differential analysis about 15 seconds after the addition of the lytic reagent composition. The sample is thereafter analyzed in an experimental hematology instrument.

| | |
|---|---|
| 1. Tergitol NP-13 (Union Carbide, ethoxylated nonylphenol) | 1.0 g |
| 2. Sodium tetradecylsulfate | 1.0 g |
| 3. Hetoxol STA30 (Heterene) | 10.0 g |
| 4. Formic acid | 0.2ml |
| 5. Sodium sulfate | 9.0 g |
| 6. Potassium chloride | 5.0 g |
| 7. Pluronic 10R5 | 15.0 g |
| 8. Deionized water | adjusted to 1L |
| 9. pH (adjusted by 4M HCl) | 2.2 |

EXAMPLE IV

First Example of the Second Lytic Reagent

A lytic reagent composition encompassing the ethoxylated long chain amine compound has been formulated with the following composition:

A cationic ethoxylated long chain amine compound with formula:

where m+n has a value of 30, was dissolved in deionized water at a concentration of 20 g/L. Formic acid was used to adjust the pH to 3.2. In addition, the following preservatives were added: 0.2 g/L EDTA, 0.5 g/L Proclin 300 (Rohm & Haas Co.), and 0.05 g/L 2,6-Di-tert-butyl-4-methylphenol (predissolved in ethanol).

EXAMPLE V

Second Example of the Second Lytic Reagent

A lytic reagent composition encompassing the polyoxyethylene based surfactant has been formulated with the following composition:

A polyoxyethylene based surfactant with formula:

$C_{18}H_{37}ZO(CH_2CH_2O)_nH$
where n is 30, was dissolved in deionized water at a concentration of 20 g/L. 0.8 g/L of sodium dodecylsulfate (SDS, Aldrich) was added. Formic acid was used to adjust the pH to 2.8.

The second lytic reagent is used in conjunction with a stabilizing reagent to form a lytic reagent system that separates the leukocytes into the lymphocyte, monocyte, basophil and granulocytes other than basophil subpopulation. An example of the stabilizing reagent is described in Example VI.

EXAMPLE VI

Stabilizing Reagent for the Second Lytic Reagent

A stabilizing reagent has been formulated as described above and is comprised of 14 g/L of NaCl, 32 g/L of $Na_2SO_4$, and 6.6 g/L of $Na_2CO_3$ buffer, pH adjusted to 11.0. The osmolality of this reagent is about 1080 mOsm.

EXAMPLE VII

Differentiation of Leukocyte Populations of a Blood Sample

To 28 ml of an EDTA-anti-coagulated normal whole blood sample, 488 ml of the lytic reagent composition of Example IV was added and the mixture was gently mixed by swirling for 4 seconds at room temperature (approximately 21° C.). The lysing reaction was retarded by the addition 209 uL of the stabilizing reagent of Example VI. The blood mixture was gently mixed and was ready for differential analysis about 15 seconds after the addition of the stabilizing agent. The final blood mixture was kept at neutral pH (about 7)and in hypertonic conditions with an osmolality about 445 mOsm. FIG. 4 shows a differential analysis using DC and RF.

While certain representative embodiments and details have been shown for the purpose of illustrating the invention, various changes and modifications can be made therein without departing from the scope of the invention as defined in the appended claims.

What is claimed is:

1. An aqueous lytic reagent composition comprising:
   a.) an alkali metal salt of alkyl sulfates,
   b.) an acid,
   c.) an eosinolytic agent that facilitates selective shrinkage of eosinophil subpopulation of leukocytes selected from the group consisting of organic phosphate esters, alkali metal salts of the organic phosphate esters, ethoxylated phosphate esters, ethoxylated mercaptans, ethoxylated lanolin alcohols, ethoxylated alkyl phenols, ethoxylated alkyl and alkenyl alcohols and mixtures thereof,
   d.) a nonionic surfactant that protects neutrophil subpopulation of leukocytes from lysis, and
   e.) a physiological salt sufficient to adjust the osmolality of said lytic reagent composition between 370 to 720 mOsm.

2. The lytic reagent composition of claim 1, wherein the alkyl group of the alkali metal salt of alkyl sulfates has 10 to 18 carbon atoms.

3. The lytic reagent composition of claim 1, wherein said alkali metal salt of alkyl sulfates in the lytic reagent composition is at a concentration from about 0.02% to about 0.16% (w/v).

4. The lytic reagent composition of claim 1, wherein the acid used adjusts pH of the lytic reagent from about 1.4 to about 3.4.

5. The lytic reagent composition of claim 1, wherein the acid comprises an organic acid, an inorganic acid, and mixtures thereof.

6. The lytic reagent composition of claim 5, wherein the acid is selected from the group consisting of citric acid, acetic acid, formic acid, propionic acid, hydrochloric acid, phosphoric acid, sulfuric acid and mixtures thereof.

7. The lytic reagent composition of claim 1, wherein said eosinolytic agent has a hydrophile lipophile balance less than about 15.

8. The lytic reagent composition of claim 1, wherein said eosinolytic agent has a concentration ranging from 0.05% to 0.8% (w/v).

9. The lytic reagent composition of claim 1, wherein said nonionic surfactant that protects neutrophil subpopulation of leukocytes from lysis comprises an ethoxylated alkyl alcohol having at least a hydrophile lipophile balance of 16, an ethoxylated alkylene alcohol having at least a hydrophile lipophile balance of 16 and mixtures thereof.

10. The lytic reagent of claim 9, wherein the concentration of the nonionic surfactant ranges from about 0.5 to 3.0% w/v).

11. The lytic reagent composition of claim 1, which further includes polyoxyethylene and polyoxypropylene copolymers in an amount sufficient to facilitate dissolving of red blood cell debris.

12. The lytic reagent composition of claim 1, wherein said physiological salt comprises alkali metal salts of chloride, alkali metal salts of sulfate, and mixtures thereof.

13. The lytic reagent composition of claim 12, wherein the concentration of the alkali metal salts of chloride is from about 0.2% to about 1.3% (w/v).

14. The lytic reagent composition of claim 12, wherein the concentration of the alkali metal salts of sulfate is from about 0.4% to about 2.0% (w/v).

15. A method for lysis of red blood cells in a blood sample and analysis of the remaining leukocyte subpopulations comprising:
   a.) exposing a blood sample to a lytic reagent composition for a time sufficient to lyse red blood cells and differentiate at least one leukocyte subpopulation in said blood sample, said lytic reagent comprising:
      1.) an alkali metal salt of alkyl sulfates,
      2.) an acid, 3.) an eosinolytic agent that facilitates the selective shrinkage of eosinophil subpopulation of leukocytes selected from the group consisting of organic phosphate esters, alkali metal salts of the organic phosphate esters, ethoxylated phosphate esters, ethoxylated mercaptans, ethoxylated lanolin alcohols, ethoxylated alkyl phenols, ethoxylated alkyl and alkenyl alcohols and mixtures thereof, 4.) a nonionic surfactant that protects neutrophil subpopulation of leukocytes from lysis, and 5.) a physiological salt sufficient to adjust the osmolality of said lytic reagent composition between 370 to 720 mOsm, b.) differentiating at least one leukocyte subpopulation selected from the group consisting of eosinophils, lymphocytes, monocytes, and neutrophils by using at least two types of measurements selected from the group consisting of DC, RF, and light scatter measurements, and c.) reporting results of said differentiation.

16. The method of claim 15, wherein time sufficient to lyse red blood cells and differentiate at least one leukocyte subpopulation in said blood sample is from approximately 10 to 25 seconds.

17. The method of claim 15, wherein the lysing of the red blood cells and differentiating of at least one leukocyte subpopulation in said blood sample is at room temperature.

18. The method of claim 17, wherein the room temperature is from approximately 15° to 30° C.

19. The method of claim 15, wherein said at least one leukocyte subpopulation is the eosinophil subpopulation.

20. The method of claim 15, wherein said at least one leukocyte subpopulation is the neutrophil subpopulation.

21. The method of claim 15, wherein said differentiating is performed by using DC and RF measurements.

22. A method for lysis of red blood cells in a blood sample and analysis of the remaining leukocyte subpopulations comprising:

a.) treating a first aliquot of a blood sample with a first lytic reagent composition for a time sufficient to lyse red blood cells and to enable detection of at least one leukocyte subpopulation in said blood sample, b.) treating a second aliquot of said blood sample with a second lytic reagent system sufficient to lyse red blood cells and to enable detection of four leukocyte subpopulations comprising lymphocytes, monocytes, basophils and granulocytes other than basophils in said blood sample, c.) analyzing the first aliquot of said treated blood using DC and RF measurements, to obtain detection of at least one leukocyte subpopulation, d.) analyzing the second aliquot of said treated blood using DC and RF measurements to obtain detection of four leukocyte subpopulations comprising lymphocytes, monocytes, basophils and granulocytes other than basophils, and e.) using the results of steps c and d to report at least five subpopulations of leukocytes.

23. The method of claim 22, wherein the time sufficient to lyse red blood cells and to enable detection of at least one leukocyte subpopulation in said first aliquot of said blood sample is from approximately 10 to 25 seconds.

24. The method of claim 23, wherein the time sufficient to lyse red blood cells in said second aliquot of said blood sample is less than approximately 10 seconds.

25. The method of claim 22, wherein the lysing of the red blood cells and detection of leukocyte subpopulations in said first and second aliquots of said blood sample are at room temperature.

26. The method of claim 25, wherein the room temperature is from approximately 15° to 30° C.

27. The method of claim 22, wherein said analyzing of the first aliquot of said treated blood using DC and RF measurements differentiates the eosinophil subpopulation.

28. The method of claim 22, wherein the first lytic reagent composition comprises:

a.) an alkali metal salt of alkyl sulfates, b.) an acid, c.) an eosinolytic agent that facilitates selective shrinkage of eosinophil subpopulation of leukocytes selected from the group consisting of organic phosphate esters, alkali metal salts of the organic phosphate esters, ethoxylated phosphate esters, ethoxylated mercaptans, ethoxylated lanolin alcohols, ethoxylated alkyl phenols, ethoxylated alkyl and alkenyl alcohols and mixtures thereof, d.) a nonionic surfactant that protects neutrophil subpopulation of leukocytes from lysis, and e.) a physiological salt sufficient to adjust the osmolality of said first lytic reagent composition between 370 to 720 mOsm.

29. The method of claim 22, wherein the second lytic reagent system comprises:

a.) a lytic reagent comprising an ethoxylated long chain amine compound represented by the general formula:

wherein R is an alkyl, alkenyl or alkynyl group having 12 to 22 carbon atoms, m and n are each 1 or more and m+n is between 20 and 40; and an acid to adjust the pH of the lytic reagent to be within the range of 2.0 to 3.6, and b). a hypertonic, alkaline stabilizing reagent composition.

30. The method of claim 22 wherein the second lytic reagent system comprises:

a.) a lytic reagent comprising a polyoxyethylene based surfactant for the determination of four leukocyte subpopulations in a blood sample comprising lymphocytes, monocytes, basophils and granulocytes other than basophils represented by the general formula:

wherein $R_1$ is an alkyl, alkenyl or alkynyl group having 10 to 22 carbon atoms, $R_2$ is —O— or —COO—, and n is between 20 and 35; and an acid to adjust the pH of the lytic reagent to be within the range of 2.0 to 4.0, and b.) a hypertonic, alkaline stabilizing reagent composition.

31. The method of claim 30, wherein the second lytic reagent system further comprises the addition of sodium dodecyl sulfate.

* * * * *